(12) United States Patent
Avitan

(10) Patent No.: US 10,772,695 B2
(45) Date of Patent: Sep. 15, 2020

(54) GLOVE WITH MEDICINAL PADS AND DIFFERING THICKNESS REGIONS

(71) Applicant: Henny Avitan, Fair Lawn, NJ (US)

(72) Inventor: Henny Avitan, Fair Lawn, NJ (US)

( * ) Notice: Subject to any disclaimer, the term of this patent is extended or adjusted under 35 U.S.C. 154(b) by 0 days.

(21) Appl. No.: 16/731,536

(22) Filed: Dec. 31, 2019

(65) Prior Publication Data

US 2020/0129257 A1    Apr. 30, 2020

(51) Int. Cl.
*A61B 42/10* (2016.01)
*A41D 19/015* (2006.01)
*A41D 19/00* (2006.01)

(52) U.S. Cl.
CPC .......... *A61B 42/10* (2016.02); *A41D 19/0024* (2013.01); *A41D 19/0037* (2013.01); *A41D 19/0068* (2013.01); *A41D 19/01594* (2013.01); *A41D 2400/32* (2013.01)

(58) Field of Classification Search
CPC .............. A61B 42/10; A41D 19/01594; A41D 19/0037; A41D 19/0024; A41D 19/0068; A41D 2400/32
See application file for complete search history.

(56) References Cited

U.S. PATENT DOCUMENTS

| | | | |
|---|---|---|---|
| 3,814,095 A * | 6/1974 | Lubens | A61K 9/703 604/307 |
| 4,864,661 A | 9/1989 | Gimbel | |
| 4,924,530 A | 5/1990 | Tagaya | |
| 4,942,626 A | 7/1990 | Stern | |
| 5,117,509 A * | 6/1992 | Bowers | A41D 19/01547 2/161.1 |
| 5,187,815 A * | 2/1993 | Stern | A61B 42/10 2/16 |
| 5,323,490 A | 6/1994 | Yarbrough | |
| 5,407,685 A * | 4/1995 | Malchesky | A01N 25/34 2/16 |
| 5,428,841 A | 7/1995 | Stein | |
| 5,614,202 A * | 3/1997 | DeFina | A41D 19/0055 424/400 |
| 5,687,424 A * | 11/1997 | Masley | A41D 19/01547 2/163 |
| 5,879,771 A * | 3/1999 | Kypreos | A41D 13/087 132/73.5 |
| 6,016,571 A * | 1/2000 | Guzman | A41D 19/0055 15/227 |

(Continued)

*Primary Examiner* — Khaled Annis
(74) *Attorney, Agent, or Firm* — Michael J. Feigin, Esq.; Feigin and Fridman LLC

(57) ABSTRACT

A glove with thinner and thicker parts is disclosed. The thinner parts, in one version of the glove, cover all of a thumb and index finger and a distal phalanx of a middle and ring finger. The rest of the glove, in such an embodiment, is thicker. The thicker parts can include the palm and dorsal side of the hand. The thinner region palmar side of the distal phalanx of the middle and ring finger include, in embodiments of the disclosed technology, a pad with a peelable cover which reveals a local anesthetic and disinfectant. Such pads can further be used/attached with a version of the glove with only thinner material throughout. In this manner, one can grasp with greater dexterity with the thinner regions of the glove compared to the thicker regions and also use a disinfectant followed by an anesthetic.

14 Claims, 5 Drawing Sheets

(56) References Cited

U.S. PATENT DOCUMENTS

| | | | | |
|---|---|---|---|---|
| 6,055,669 | A * | 5/2000 | Albert | A63B 71/148 2/161.1 |
| 6,168,800 | B1 * | 1/2001 | Dobos | A61L 15/24 424/405 |
| 6,604,244 | B1 * | 8/2003 | Leach | A41D 19/0055 15/227 |
| 7,020,898 | B1 * | 4/2006 | Pucci | A01K 13/001 2/161.6 |
| 10,064,389 | B2 * | 9/2018 | Schuster | A46B 5/04 |
| 10,117,558 | B1 * | 11/2018 | Restrepo | A47L 17/00 |
| 10,549,404 | B1 * | 2/2020 | Norton | B24D 15/045 |
| 2003/0056274 | A1 | 3/2003 | Sorrels | |
| 2005/0132467 | A1 * | 6/2005 | Tippey | A41D 19/0055 2/159 |
| 2005/0193464 | A1 * | 9/2005 | Hess | A41D 19/01582 2/160 |
| 2007/0083980 | A1 * | 4/2007 | Yang | A41D 19/0068 2/167 |
| 2007/0137812 | A1 * | 6/2007 | Shannon | D21H 27/008 162/109 |
| 2007/0240247 | A1 * | 10/2007 | Beck | A01N 25/34 2/16 |
| 2008/0132908 | A1 | 6/2008 | Nguyen | |
| 2008/0227055 | A1 * | 9/2008 | Seidman | A41D 19/0024 433/141 |
| 2008/0282446 | A1 | 11/2008 | Komlos | |
| 2009/0013441 | A1 * | 1/2009 | Duffy | A41D 13/087 2/21 |
| 2011/0047672 | A1 * | 3/2011 | Hatfield | A41D 19/0024 2/163 |
| 2011/0306942 | A1 * | 12/2011 | Thorpe | A61M 35/10 604/289 |
| 2013/0025327 | A1 * | 1/2013 | Cornish | A41D 19/02 66/174 |
| 2013/0139294 | A1 | 6/2013 | Zetune | |
| 2013/0213094 | A1 * | 8/2013 | Moreland | D04B 1/28 66/174 |
| 2014/0059739 | A1 * | 3/2014 | Gellis | A41D 19/0048 2/168 |
| 2014/0237701 | A1 * | 8/2014 | Thompson | A41D 19/001 2/164 |
| 2015/0289576 | A1 * | 10/2015 | Woody | A41D 19/0024 2/16 |
| 2017/0142931 | A1 * | 5/2017 | Michaelson | A46B 5/04 |
| 2018/0093083 | A1 * | 4/2018 | Headington | A41D 19/0024 |
| 2018/0199644 | A1 * | 7/2018 | Sando | A41D 19/0096 |
| 2018/0229275 | A1 * | 8/2018 | Gracie | A01G 22/00 |
| 2018/0296058 | A1 * | 10/2018 | Firouzman | A47L 13/18 |
| 2018/0360142 | A1 * | 12/2018 | Barton | A41D 19/0037 |

\* cited by examiner

GLOVE WITH MEDICINAL PADS AND DIFFERING THICKNESS REGIONS

FIELD OF THE DISCLOSED TECHNOLOGY

The disclosed technology relates generally to a glove with varying thickness portions thereof, and more specifically, to a glove with some thinner finger and finger tips.

The disclosed technology further relates to medicinal pads on finger tips of a glove, and more specifically, to protected pads with disinfectants and medicine.

BACKGROUND OF THE DISCLOSED TECHNOLOGY

Latex and non-latex surgical gloves are quite commonly found in hospitals, doctors offices, and other places for medical use. On the one hand, they should be thick enough so as to be able to handle medical procedures including rubbing against a patient's skin and teeth while also handling sometimes sharp objects such as scalpels and knives. A breakage comprises the sterility of a medical procedure and can harm the health of the medical caregiver as well as others that this caregiver later administers care thereto. Thicker gloves are stronger but provide less dexterity and ability to feel the patient. Thinner gloves provide greater dexterity and feel of what is outside of the glove, but are more likely to puncture.

Prior technology has attempted to solve this issue by, for example, providing puncture resistant areas of a glove with thicker material such as is found in U.S. Pat. No. 4,864,661 to Gimbel, U.S. Pat. No. 5,428,841 to Stein, U.S. Pat. No. 4,952,626 to Stern, and others. Some prior technology takes an "opposite" approach by providing a glove with some thinner areas of greater dexterity, such as U.S. Pat. No. 4,924,530 to Tagaya and U.S. Patent Publication 2008/0282446 to Komlos.

While these inventions help in various circumstances, caregivers often have to handle many tasks which require different amounts of dexterity and grabbing of different types of objects and medications at different times. Thus, there remains a need in the art to provide greater ability to have the safety of a glove while also have a greater ability to give care.

SUMMARY OF THE DISCLOSED TECHNOLOGY

A glove (a flexible and resilient device shaped to fit over a human hand with an opening at the wrist and separate extensions for each digit of the hand) of embodiments of the disclosed technology has an exterior which forms the outer boundaries thereof. This exterior has both a flexible thinner portion and a flexible thicker portion, relative to one another. The thicker portion can be instead of the thinner portion or can include the thinner portion with an extra layer or extra thickness formed from a single mold or piece of material. The thinner portion (where "thinner" is used to describe where this is only a thinner exterior which lacks what is herein described as "thicker" in this disclosure) of the glove corresponds to one or more of an index finger, thumb, and distal phalanx of a middle and/or ring finger and/or any other finger. This can include some or all of the thumb and index finger and/or at least a majority there of (wherein "majority" is defined as 51% or more).

Peelable pads cover some of the thinner portions of the glove, in embodiments of the disclosed technology, such as a palmar side (a lower side/side of the hand where the palm of the hand is situated) thereof. More specifically, the pad or pads can cover a majority of a distal phalanx, such as that of the middle or ring finger. This can be so in a glove with only a "thinner" material or one which has some thinner coverage and some thicker coverage of the hand. The thinner material can be material which is 4, 5, 6, 7, 8, or just under 9 microns thick. The thicker material can be material which is 9, 10, 11 or more microns thick. The thinner portion can be half as thick as the thicker portion, one quarter as thick as the thicker portion, and any amount there between as needed for a particular application.

The pads can have two parts: a) a peelable cover which is removable therefrom, b) a portion underneath the peelable cover which has sponge qualities (can retain liquid, releases at least some liquid when squeezer) or which has a liquid material. The liquid material can be a local anesthetic (e.g. procaine or lidocaine) or a disinfectant (e.g. isopropyl alcohol). The pads can cover a majority of, or a large majority (75%+) of the distal phalanx of one of the digits of the hand. One can then manipulate (defined as move, compress, add a substance to) skin of a patient using the thinner portion of the glove, such as by way of using their index and/or thumb. One can then sterilize the skin using isopropyl alcohol from the palmar side of a distal phalanx of the glove and/or use a local anesthetic by way of removing a peelable cover and manipulating the skin of a patient with the local anesthetic found under the peelable portion of one of the pads.

In some embodiments, a glove specifically has a portion between 4 and 9 microns (the "thinner portion") and a portion greater than 9 microns (the "thicker portion"). The thicker portion allows from greater strength and resiliency while the thinner portion allows from greater dexterity, each portion where needed most. Resiliency and resilient are defined as the ability to maintain structural integrity and return to a prior resting state when subjected to sheer forces. Dexterity is defined as an amount of an ability to perform a task with intricate movements, where intricate movements are those which can be felt by finger tips.

The thicker portion can be on part of a glove which corresponds to (is designed to cover and/or surround) an entirety of a non-finger portions of the hand/glove (e.g. palmar and side of hand excluding the five fingers), a full finger, and parts of other fingers such as two other fingers, and further, such as the proximal phalanx and middle phalanx. The thinner layer can be on the distal phalanx of one, two, three, four, or five fingers and the middle and proximal phalanx of one, two three, four, or five fingers. The thinner portion of the distal phalanx of one, two, three, or four fingers can further have a peelable pad with a peel off layer and non-peelable pad beneath. Multiple such peelable pads can be present, one on each finger, and which can cover a majority of or substantially an entirety of a respective distal phalanx.

A glove specifically with isopropyl alcohol on a palmar side of a first distal phalanx of said glove is also part of the disclosed technology. The isopropyl alcohol is between the glove and a removable cover in this embodiment. A local anesthetic on the palmar side of a second distal phalanx of the glove is between the glove and a removable cover. The palmar side of the distal phalanxes which have removable covers are less than 9 microns thick.

It should be understood that when a glove is being described using anatomy of a person in this disclosure, this refers to a portion of the glove which is adapted to cover, corresponds to, or would be recognizable by its shape and position on the glove, a likewise-named part of the hand.

Gloves of embodiments of the disclosed technology can be made of polyurthethane or polyisoprene. It should further be understood that the more common term is sometimes used in place of the medical name, e.g. thumb instead of pollex, index finger instead of digitus secumdus manus, middle finger instead of digitus me'dius, ring finger instead of digitus annula'ris, and pinky instead of digitus mi'nimus ma'nus.

Any device or step to a method described in this disclosure can comprise or consist of that which it is a part of, or the parts which make up the device or step. The term "and/or" is inclusive of the items which it joins linguistically and each item by itself.

DETAILED DESCRIPTION OF EMBODIMENTS OF THE DISCLOSED TECHNOLOGY

A glove with thinner and thicker parts is disclosed. The thinner parts, in one version of the glove, cover all of a thumb and index finger and a distal phalanx of a middle and ring finger. The rest of the glove, in such an embodiment, is thicker. The thicker parts can include the palm and dorsal side of the hand (excluding the afore-described parts of the digits). The thinner region palmar side of the distal phalanx of the middle and ring finger include, in embodiments of the disclosed technology, a pad with a peelable cover which reveals a local anesthetic and disinfectant (one on each pad). Such pads can further be used/attached with a version of the glove with only thinner material throughout. In this manner, one can grasp with greater dexterity with the thinner regions of the glove compared to the thicker regions and also use a disinfectant followed by an anesthetic on a patient using the same hand which is presently grasping or in contact with a patient via other digits.

Embodiments of the disclosed technology will become more clear in view of the following description of the figures.

Figure 1:
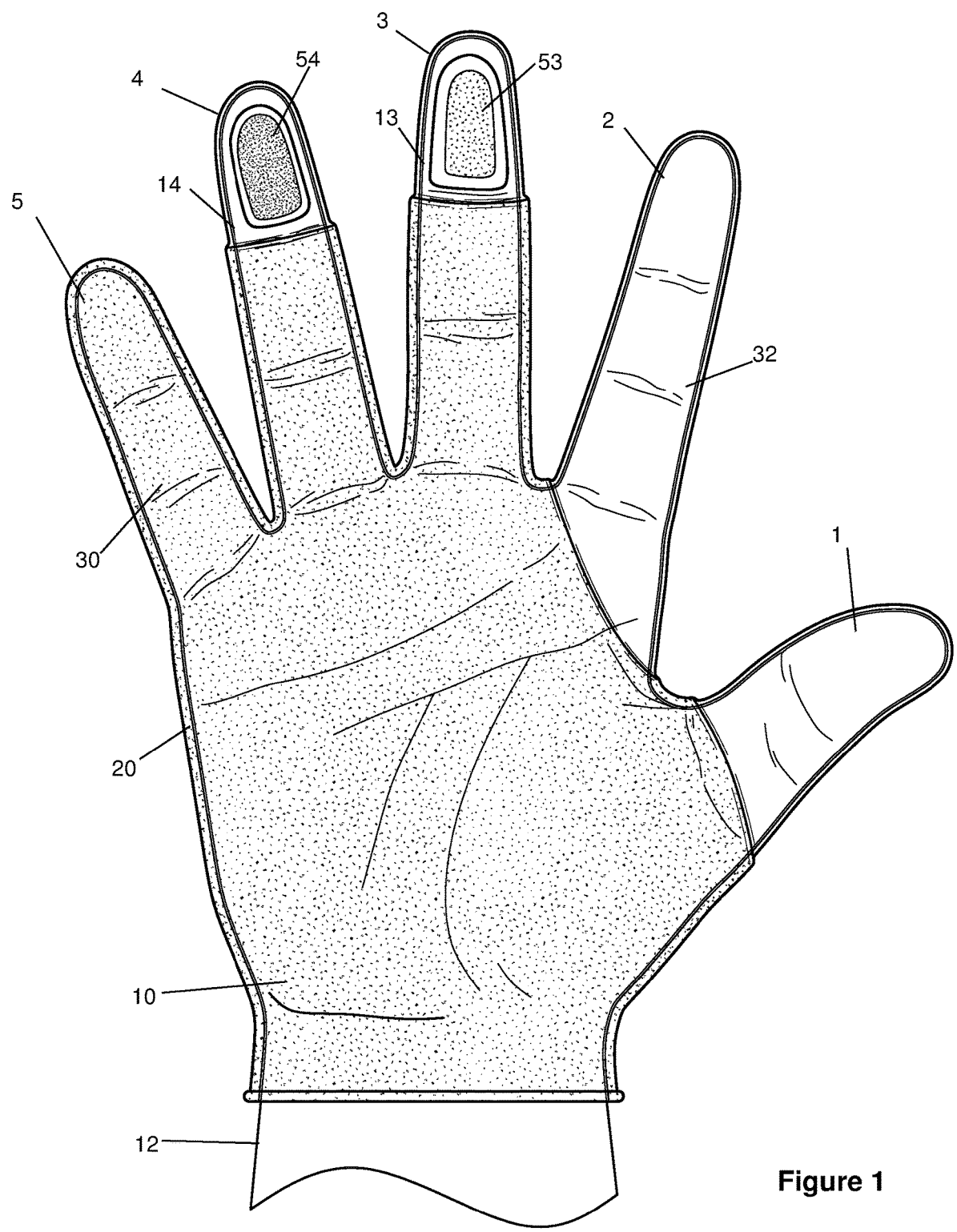
FIG. 1 shows a glove with thicker and thinner regions in an embodiment of the disclosed technology.

FIG. 1 shows a glove with thicker and thinner regions in an embodiment of the disclosed technology. A glove has digits 1, 2, 3, 4, 5 and corresponding to a thumb, index finger, middle finger, ring finger, and pinky respectively. (See the "summary" section for a link between the glove "having" anatomical parts. Such anatomical parts are with reference to the part of the glove which is designed to cover a hand which actually has such anatomical parts.) The glove has a thicker layer 30 and thinner layer 32. The layers can be separately created and then attached together or the thicker layer can be placed over the thinner layer as part of producing the glove in one stage or two separate stages.

The glove 10, in embodiments of the disclosed technology, covers a full hand and ends before a wrist 12 though a glove of any length can be used as long as it covers at least some of the fingers, all of the fingers, or more of the hand 20 (the part of the human which is the end part of the arm beyond the wrist, including the palm, fingers, and thumb.

The thicker 30 parts of the glove 10 can include the palm, back of hand, and at least some of the fingers such as an entirety of the pinky finger 5, the majority of the ring finger 4, and the majority of the middle finger 3. The fingers have proximal, middle, and distal phalanxes. In embodiments of the disclosed technology the thicker 30 regions of the glove 10 end between/at/substantially at the end of a middle phalanx of one or more fingers and the distal phalanx of the one or more fingers. Thus, the thicker 30 region covers the proximal and middle phalanx of the ring finger 4 in embodiments while the thinner region covers the distal phalanx 14 of the ring finger in some embodiments of the disclosed technology. Further, in such embodiments the thicker region 30 clovers the proximal and middle phalanx of the middle finger while the thinner region 30 covers the distal phalanx 13 of the middle finger. The thinner region can also cover the entirety of the thumb 1 and index finger 2.

Note further that there is a pad 54 on the distal phalanx 14 of the fourth finger 4 and a pad 53 on the distal phalanx 13 of the third finger 3 in embodiments of the disclosed technology. The pads 53 and 54 can be on the palmar side of the hand (the palmar side being a side of a hand with a palm and/or opposite a dorsal side of the hand or finger). The pads can take up a majority of, half of, or a minority of the palmar side of a distal phalanx. The pads 53 and 54 are discussed in more detail with respect to FIG. 3.

Figure 2:
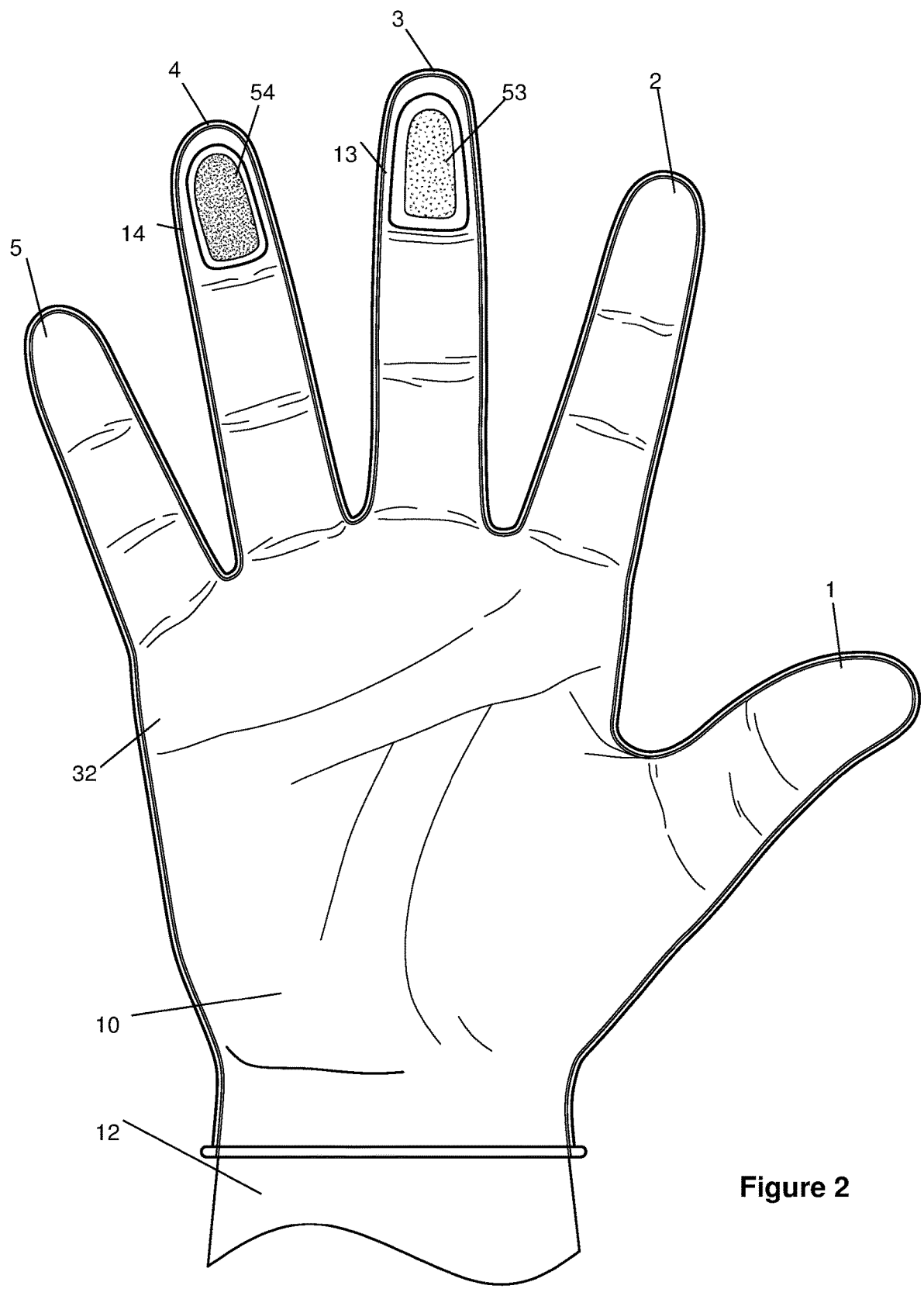
FIG. 2 shows pads on digits of a glove in an embodiment of the disclosed technology.

FIG. 2 shows pads on digits of a glove in an embodiment of the disclosed technology. In this embodiment, the entirety of the glove is in the thinner material 32 while still having the pads 53 and 54 as indicated with respect to the above description of FIG. 1. Alternatively, the entire glove can be of the thicker material. The thinner material 32 is less than 7, 8, or 9 microns, such as 4 microns wide, in embodiments of the disclosed technology. The thicker material 30 (see FIG. 1) is 8, 9, or more microns wide in embodiments of the disclosed technology so long as the thicker material is thicker than the thinner material. The thinner material allows for greater feeling sensation and dexterity at the points thereof while the thicker material is more resilient in embodiments of the disclosed technology. In some embodiments, the thicker and thinner material are simply thicker and thinner relative to one another and without a specifically limited thickness.

Figure 3:
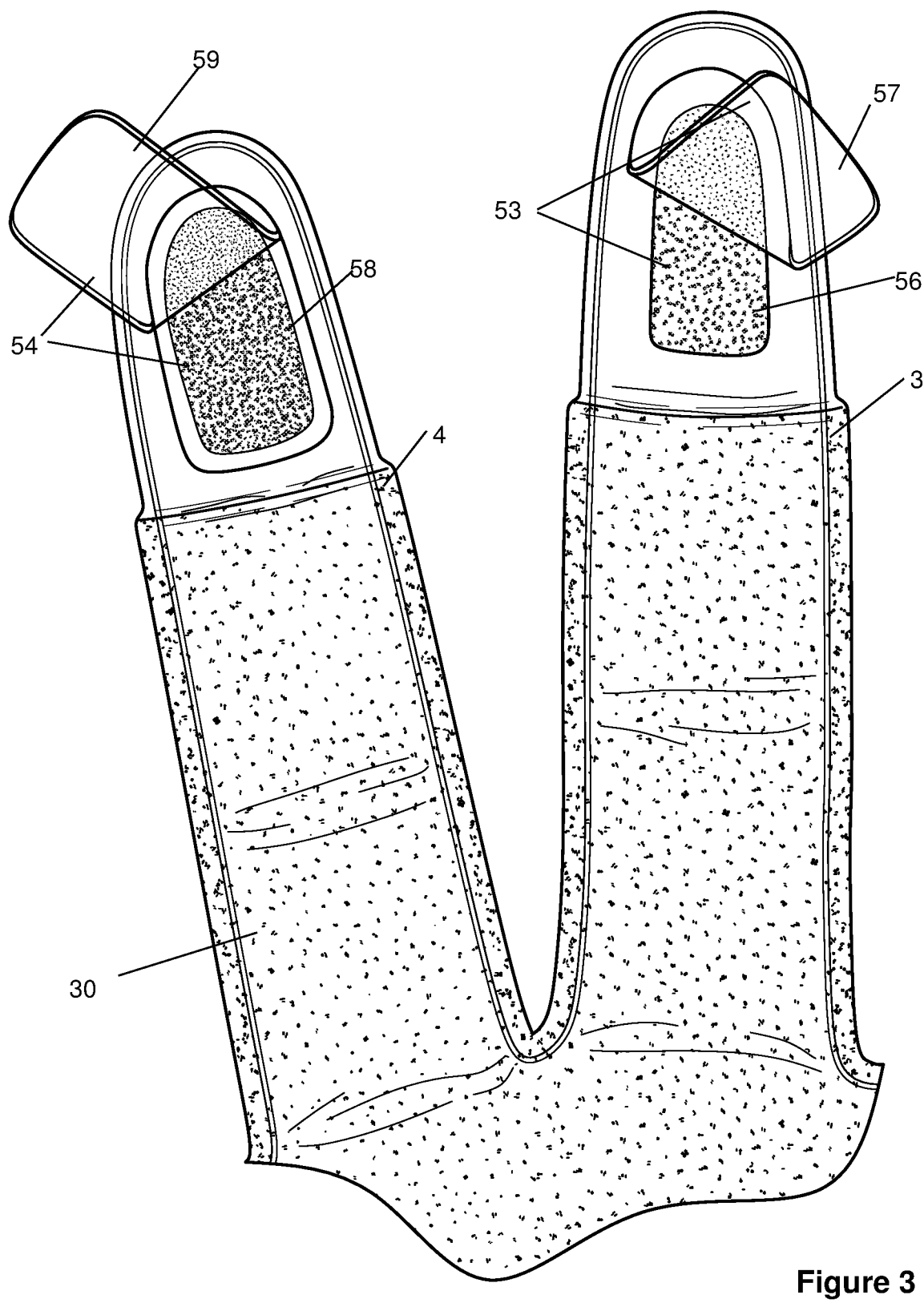
FIG. 3 shows removal of a peelable layer/cover of pads on digits of a glove in an embodiment of the disclosed technology.

FIG. 3 shows removal of a peelabe layer/cover of pads on digits of a glove in an embodiment of the disclosed technology. Here the pads 53 and 54 are seen larger with a peelable layer 59 on pad 58 and a peelable layer 57 on pad 56. "Pad" refers to the under-side and cover in general when used as such or simply the under-side when used as such. The peelable layers can be water resistant and air tight, holding the pads there-beneath in an air tight manner such that liquid or moisture on the pads 56, and 58 are held therein and prevented from evaporating or substantially prevented from evaporating. The pads 58 and 56 can hold moisture or liquid which either comes out when rubbed against a surface, such as the skin of a patient, and/or when the peelable layer there-over is removed. The pads 58 and 56 can also have sponge-like qualities whereby compressing a pad results in the excretion of liquid.

On the pad 56 of the middle finger 3 portion of the glove 10 there can be a disinfectant such as alcohol. A "disinfectant" is a chemical designed to or known to kill bacteria and/or destroy chemicals which are harmful to humans. As such, one can manipulate the skin of a patient using a thumb 1 and index finger 2, and/or place the disinfectant on the skin (or mouth interior, or other part of a patient). Then, one can peel back the cover 59 and use a substance in pad 58 to rub or place onto a patient, on the part which has been disinfected. This substance in pad 58 can be a drug such as a local anesthetic, e.g. procaine or lidocaine.

Figure 4:
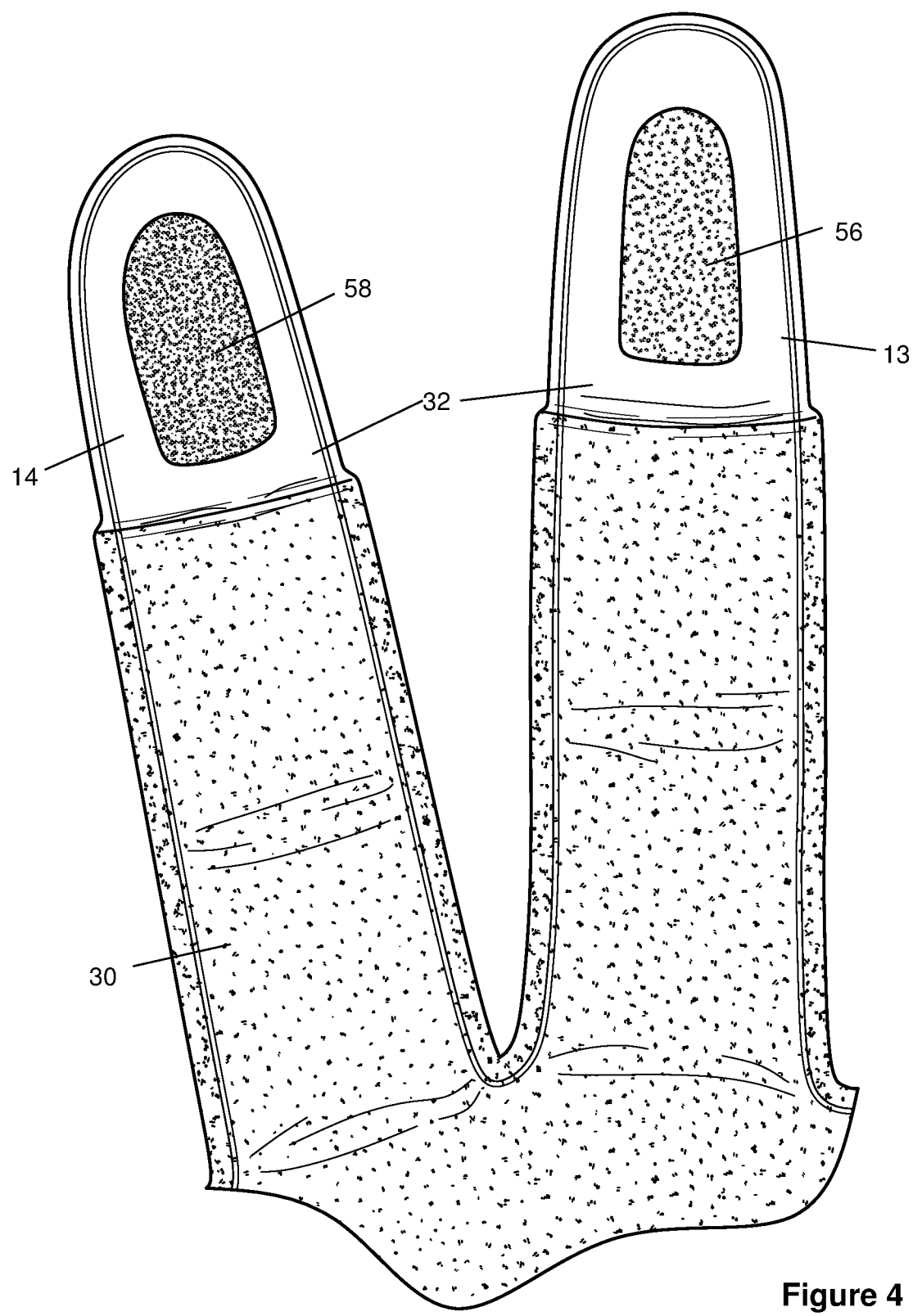
FIG. 4 shows a local anesthetic and disinfectant on respective palmar sides of distal phalanxes of a glove in an embodiment of the disclosed technology.

FIG. 4 shows a local anesthetic and disinfectant on respective palmar sides of distal phalanxes of a glove in an embodiment of the disclosed technology. Here, this is after the covers are removed and the disinfectant on pad 56 is read to be used before the local anesthetic 58. Thus, one can use the fingers in order—thumb 1 and index finger 2 to physically manipulate a patient or find an area for treatment followed by a middle finger 3 used to disinfect and then a ring finger 4 used to anesthetize.

Figure 5:
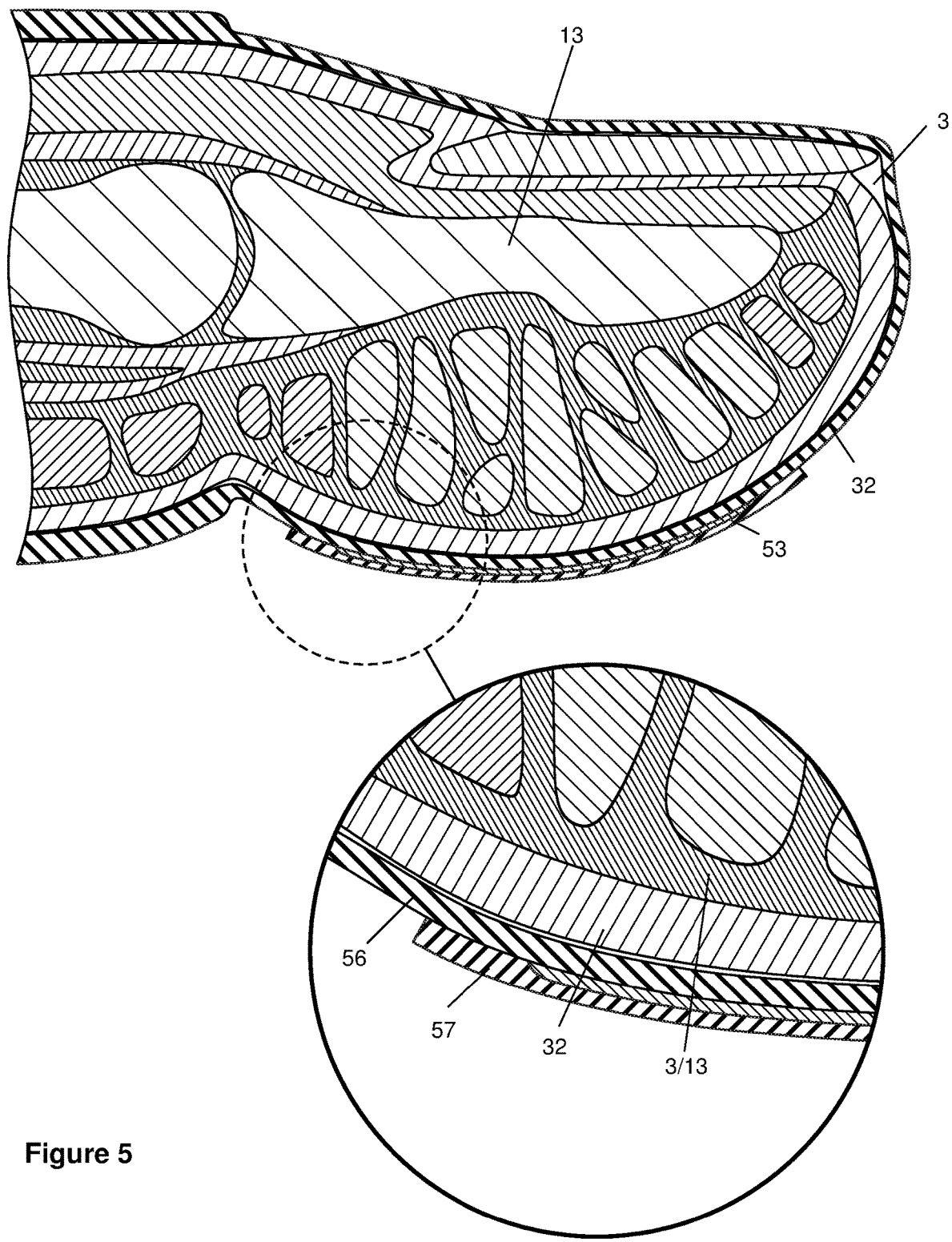
FIG. 5 shows a cutaway view of a distal phalanx of a glove and finger with pad and peelable layer/cover in an embodiment of the disclosed technology.

FIG. 5 shows a cutaway view of a distal phalanx of a glove and finger with pad and peelable layer/cover in an embodiment of the disclosed technology. Here the distal phalanx 13 (including the actual bone thereof) of the middle finger 3 is shown. On a palmar side of the tip of the finger 3 is a a pad 53 with cover. In the circular inset the layers are more visible. The thinner layer 32 of the glove 10 surrounds the finger 3 including the distal phalanx 13. The layers of the pad including the pad base 56 (or simply "pad") and cover 57 are visible one on top of the next in this order.

For purposes of this disclosure, the term "substantially" is defined as "at least 95% of" the term which it modifies.

Any device or aspect of the technology can "comprise" or "consist of" the item it modifies, whether explicitly written as such or otherwise.

When the term "or" is used, it creates a group which has within either term being connected by the conjunction as well as both terms being connected by the conjunction.

While the disclosed technology has been disclosed with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods and apparatuses described hereinabove are also contemplated and within the scope of the invention.

The invention claimed is:

1. A glove, comprising:
a flexible thinner portion of said glove;
a flexible thicker portion of said glove relative to said thinner portion of said glove;
wherein said thinner portion corresponds to at least substantially all of an index finger and substantially all of a middle finger;
wherein a first peelable pad covers a majority of a palmar side of said distal phalanx of said middle finger;
wherein a second peelable pad covers a majority of a palmar side of said distal phalanx of a ring finger;
wherein said thinner portion lacks covering by said thicker portion when formed.

2. The glove of claim 1, wherein a layer of isopropyl alcohol is situated between said thinner portion and said first peelable pad of said distal phalanx.

3. The glove of claim 1, wherein a layer of a local anesthetic is situated between said thinner portion and said second peelable pad.

4. The glove of claim 3, wherein said local anesthetic is procaine or lidocaine.

5. The glove of claim 3, wherein:
patient skin is manipulated using said thinner portion of said glove corresponding to a thumb and index finger;
said patient skin is sterilized using isopropyl alcohol on said palmar side of said distal phalanx of said glove.

6. The glove of claim 1 wherein said thinner portion has a thickness less than 9 microns thick.

7. The glove of claim 6, wherein said thicker portion has a thickness greater than 9 microns thick.

8. A glove with two different thickness portions:
a thinner portion having a thickness at least a quarter as thick as that of a thicker portion;
said thicker portion having a thickness greater than 9 microns;
wherein said thicker portion corresponds to at least an entirety of non-finger portions of said glove and at least one full finger; and
said thinner portion corresponds to substantially an entirety of a thumb and index finger as well a distal phalanx of at least one other finger, a palmar side thereof said at least one other finger having a first removable pad; and
said thicker portion is separate from and attached to said thinner portion; and
wherein a second peelable pad covers a majority of a palmar side of said distal phalanx of a ring finger.

9. The glove of claim 8, wherein said thinner portion of at least a second other finger, having a second removable pad on a palmar side thereof.

10. The glove of claim 8, wherein said thinner portion further corresponds to a distal phalanx corresponding to a ring finger has a second peelable pad.

11. The glove of claim 10, wherein said first peelable pad is removable to reveal a local anesthetic.

12. The glove of claim 11, wherein said second peelable pad is removable to reveal a disinfectant.

13. The glove of claim 8, wherein said at least one full finger with said thicker finger is a pinky.

14. A glove with:
isopropyl alcohol on a palmar side of one of a middle finger or ring finger-of said glove, said isopropyl alcohol between said glove and a removable cover;
a local anesthetic on said palmar side of another of said ring finger or middle finger of said glove, said local anesthetic between said glove and a removable cover;
wherein said palmar side of said index finger and said thumb are thinner than an entirety of pinky finger.

* * * * *